United States Patent
Tseng

(10) Patent No.: US 6,723,380 B2
(45) Date of Patent: Apr. 20, 2004

(54) METHOD OF MAKING A COMPOUND PRECURSOR BY COATING

(75) Inventor: How Tseng, Taipei (TW)

(73) Assignee: Biotech One Inc., Taipei (TW)

( * ) Notice: Subject to any disclaimer, the term of this patent is extended or adjusted under 35 U.S.C. 154(b) by 27 days.

(21) Appl. No.: 10/212,695

(22) Filed: Aug. 7, 2002

(65) Prior Publication Data

US 2003/0190418 A1 Oct. 9, 2003

(30) Foreign Application Priority Data

Apr. 3, 2002 (TW) .................... 91106705 A

(51) Int. Cl.[7] .............. B05D 7/22; B05D 3/02; B05D 3/12; B05D 1/02
(52) U.S. Cl. .............. 427/212; 427/222; 427/240; 427/421; 427/427; 427/376.1; 427/2.24; 427/2.26; 427/2.1
(58) Field of Search ................ 427/212, 222, 427/240, 421, 427, 376.1, 2.24, 2.26, 2.1

(56) References Cited

U.S. PATENT DOCUMENTS

| 5,366,756 A | * | 11/1994 | Chesterfield et al. ...... 427/2.26 |
| 5,747,390 A | * | 5/1998 | Cooper et al. ............... 442/59 |
| 6,344,209 B1 | * | 2/2002 | Saito et al. ................ 424/426 |

* cited by examiner

Primary Examiner—Michael Barr
(74) Attorney, Agent, or Firm—Bacon & Thomas, PLLC

(57) ABSTRACT

The present invention is to provide a method of making a polymer compound material by coating an inorganic material on the surface of a polymer. The method provided by the present invention comprises the step of spraying a high volatile solvent to a chipped polymeric matrix to slightly dissolve the surface of the matrix, and the step of adding inorganic material powders to let the powders be coated on the surface of the matrix layer by layer so as to form the polymer compound material.

18 Claims, 5 Drawing Sheets

METHOD OF MAKING A COMPOUND PRECURSOR BY COATING

FIELD OF THE INVENTION

The present invention relates to a method of making a compound precursor and, more particularly to a method of making a compound precursor by coating in which a solvent is sprayed onto a polymeric matrix to slightly dissolve the surface of the polymeric matrix, and then a powdered inorganic reinforced filler is coated onto the surface-dissolved matrix, forming the desired compound precursor.

BACKGROUND OF THE INVENTION

When the hard tissue of a living being is damaged or the bond defect caused by injuring disease is happened, it takes a long time to repair the tissue and the bond defect, or the reproduction of the tissue and the bond defect may be not possible. Therefore, many researches use synthesized or processed biomaterials to substitute for damaged hard tissue, recovering the functioning of the tissue. Poly-L-lactide is commonly used as a substitute for human bones.

Polylactide is a biocompatible and biodegradable copolymer. Subject to structure of the polylactide, polylactide includes crystalline poly-L-lactide and poly-D,L-lactide and amorphous poly-D-lactide. Natural lactide in living beings is of L type, thus L type polylactide and D,L type polylactide are commonly used for making biomaterial for use in human beings. Polylactide is degraded to lactic acid by hydrolysis and deesterification, lactic acid is oxidized into pyruvate under the presence of lactate dehydrogenase, and then pyruvate is metabolized into carbon dioxide and water by means of Kreb's cycle, and then discharged out of the body through the lungs and the kidneys (Hollinger & Battistone, 1986; Kulkarni et al., 1966). When using polylactide to make biomaterial for use as a substitute for bones, the mechanical strength must be strong enough to bear external force. In order to enhance the mechanical strength of polylactide-matrix biomaterial, ceramic material of hydroxyapatite may be composed to the polylactide-matrix.

Hydroxyapatite [$Ca_{10}(PO_4)_6(OH)_2$] is the main ingredient of the teeth and bones of the body of a human being, which is intensively used in medical implant materials and chromatography (protein purification and DNA separation) (P. Luo & T. G. Nieh, 1996), and has proper strength and osteoconductivity (Verheyen et al., 1992). Among biomaterials, hydroxyapatite is a calcium phosphate ceramic material commonly used for repairing the hard tissue defects. Hydroxyapatite in living beings will be affected by the pH value of the living beings. Different pH values produce different effects to the dissolution of hydroxyapatite. It will cause the dissolution of hydroxyapatite if the pH value is lower than 4.2 and/or there exists $CO_3^-$, $Sr^{2+}$ or $Mg^{2+}$. Hydroxyapatite is soluble in acid environment. Hydroxyapatite is a hard but fragile material having a relatively higher Young's modulus and lower extensibility. The hard material property of hydroxyapatite can improve the strength of hydroxyapatite/polylactide composite and extend its strength maintaining time. According to U.S. Pat. No. 6,232,384B1, the initial bending strength of hydroxyapatite/polylactide compound is greater than 250 MPa, which lasts for as long as 3 months in a living being and, starts to degrade and to be absorbed 6 months ~3 years thereafter (Hyon, 2001).

Hydroxyapatite/polylactide composites are commonly made by solution-mixing method. KEMAL KESENCİ et al. made an experiment in 2000 to produce hydroxyapatite/polylactide composites with hydroxyapatite and poly-L-lactide as matrix by means of precipitation in solution. KEMAL KESENCİ et al. obtained poly-L-lactide by means of ring-opening polymerization. Poly-L-lactide was dissolved in chloroform, and mixed with hydroxyapatite at different ratios. When well mixed, mixed solution was dried. The product thus obtained was then treaded through a series of procedures including heat pressing, temperature lowering, storing, etc. to obtain final product of hydroxyapatite/polylactide composites (KEMAL KESENCİ et al., 2000). Except solution-mixing method, Törmälä et al., 1992 mentioned, in U.S. Pat. No. 5,084,051, several composite preparation methods as outlined hereinafter:

A. Cover bioabsorbable polymer membrane on bioceramics (size: 30×10 $mm^2$), put a heating board on the polymer membrane and start heat pressing to mount polymer membrane on bioceramics. The thickness of polymer membrane is about 1 mm. The compound material thus obtained is cooled to room temperature under the presence of a pressure.

B. Put reinforced fibers on bioceramics, then cover a layer of polymer membrane (thickness about 2 mm) on reinforced fibers, heat press the layer of polymer membrane, causing reinforced fibers and polymer membrane to be melted and adhered to the inside of bioceramics. The compound material thus obtained is cooled to room temperature under the presence of a pressure.

C. Apply a polymer-dissolved solvent to the surface of bioceramics, and then repeat the procedure after the solvent transited into vapor. The procedure is repeated again and again until the thickness of the coated polymer reached 0.5 mm.

D. Put reinforced fibers onto bioceramics, and then apply a polymer solution to the boundary between reinforced fibers and bioceramics, and then cover a Teflon sheet on the top, and then apply a pressure to the Teflon sheet against reinforced fibers and bioceramics, and then repeat the procedure of adding polymer solution and giving a pressure after solvent of previously applied polymer solution changed into vapor. The procedure is repeated again and again until the thickness of fiber reinforced polymer reached 0.5 mm.

E. Monomer-contained solution, which is capable of polymerization, is applied to the surface of bioceramics until the thickness of polymer thus formed reached 1 mm.

F. Put reinforced fibers on bioceramics, and then apply a monomer-contained solution (solution applicable for polymerization) to the boundary between reinforced fibers and bioceramics until the thickness of fiber-reinforced polymer thus formed reached 1 mm.

U.S. Pat. No. 4,781,183 (Casey et al., 1988) mentioned two systems of composite preparation methods as follows:

A. Bioabsorbable Particulate Filled Systems:

Melt polymer matrix in nitrogen or vacuum, and add stuffing material slowly to the desired concentration.

B. Fiber Reinforced Systems:

It is also called solution impregnation and laminations and melt impregnation and laminations. Solution impregnation and laminations is to impregnate filler in a solution of the biodegradable polymer, enabling the solution to permeate into the filler, and then the impregnated filler is thoroughly dried. The well-dried filler is then heat-pressed into the desired final product. For melt impregnation and laminations, films of the biodegradable polymer are made by solvent casting or melt pressing. Alternatively, fibrous mats are made from polymer by running a solution of the polymer into a non-solvent in a thin stream to form a stringy precipitate, followed by pressing into a mat at room temperature. The films or mats are then laid between yarn or fabric layers in a mold of a predetermined thickness. Vacuum is applied to the lay-up, by vacuum-bagging the mold, and heat and compression are applied to consolidate the laminate.

The prior art methods mentioned above are still not satisfactory in function, and have numerous drawbacks as outlined hereinafter.

A. Complicated Preparation Procedure:

It takes much time to obtain the desired final product through a series of procedures including dissolving, blending, pressure giving, drying, temperature lowering, storing, and etc.

B. High Manufacturing Cost:

Because much amount of solvent and materials and many instrument and equipment are used during the fabrication, the manufacturing cost is high.

C. Not in Conformity With Environment Protection:

A big amount of waste product is produced during the fabrication, and the produced waste product tends to cause pollution.

D. Using a Big Amount of Toxic Solution:

Much solvent harmful to the health is used to dissolve polymer during blending in solution or solution impregnation and laminations. For example, dichloromethane and chloroform for dissolving poly-L-lactide are both toxic.

E. Finished Product Tending to be Contaminated:

Because the procedure is complicated and many materials are used during the procedure, finished product tends to be contaminated with these materials. When contaminated, finished product cannot be used for medical implant application.

SUMMARY OF THE INVENTION

It is the primary objective of the present invention to provide a method of making a compound precursor adapted to be further used in an injection-molding processing, an extrusion processing or the like, which is easy to perform. According to the prior art methods, it takes several days to obtain the desired final product after through a complicated series of procedures including dissolving, blending, pressuring, drying, cooling, and storing. The manufacturing process of the present invention is simple and, can be fully automatically performed. According to the present invention, it takes only few hours to obtain the desired final product. Therefore, the invention saves much labor expenses and, greatly reduces the risk of unintentional mistake of human, and ensures the quality of finished products.

It is another objective of the present invention to provide a method of making a compound precursor via coating, which is economic to perform. The method of the present invention enables the selected materials to be directly made into the desired final products efficiently. According to the conventional methods, much money should be invested to install a variety of processing equipment such as heat press, blender, heater, baking oven, etc. The invention eliminates this problem. Because the invention directly makes the selected materials into the desired final products, the manufacturing process is efficient and saves much installation cost.

It is still another objective of the present invention to provide a method of making a compound precursor via coating, which does not cause any significant environmental pollution problems. Because only a small amount of solvent is used and applied to the prepared matrix in an enclosed chamber by spraying during the manufacturing process, the invention does not cause any significant environmental pollution problems.

To achieve these objectives of the present invention, the method of making a compound precursor comprises the step of forming a biodegradable and bioabsorbable polymer material into a chipped matrix, the step of spraying a solvent to the chipped matrix to slightly dissolve the surface of the chipped matrix, and the step of coating the surface-dissolved chipped matrix thus obtained with a reinforced filler, thereby forming a heterogeneous precursor. The precursors made by the method of the present invention can be further used in an injection-molding processing, extrusion processing or the like to make biomaterial products. Because the final product is prohibited from contamination, it is suitable for bioabsorbable implant. According to conventional methods, the material preparation for obtaining a product of uniform compound by injection-molding/extrusion is complicated. The material preparation includes the procedure of obtaining homogeneous compound chips by means of mixing, glass fiber adding, and chip forming. The homogeneous compound chips are then processed into the desired final product by injection-molding or extrusion. This procedure is not suitable for processing compound materials containing degradable substances because the materials tend to be degraded during mixing and heating process, resulting in poor physical properties of finished products. The compound precursor made according to the present invention is heterogeneous suitable for processing into the desired final homogeneous compound products through injection-molding or extrusion. Because the invention eliminates a heating procedure, the method of the invention does not cause degradation of the materials.

DETAILED DESCRIPTION OF THE INVENTION

Figure 1:
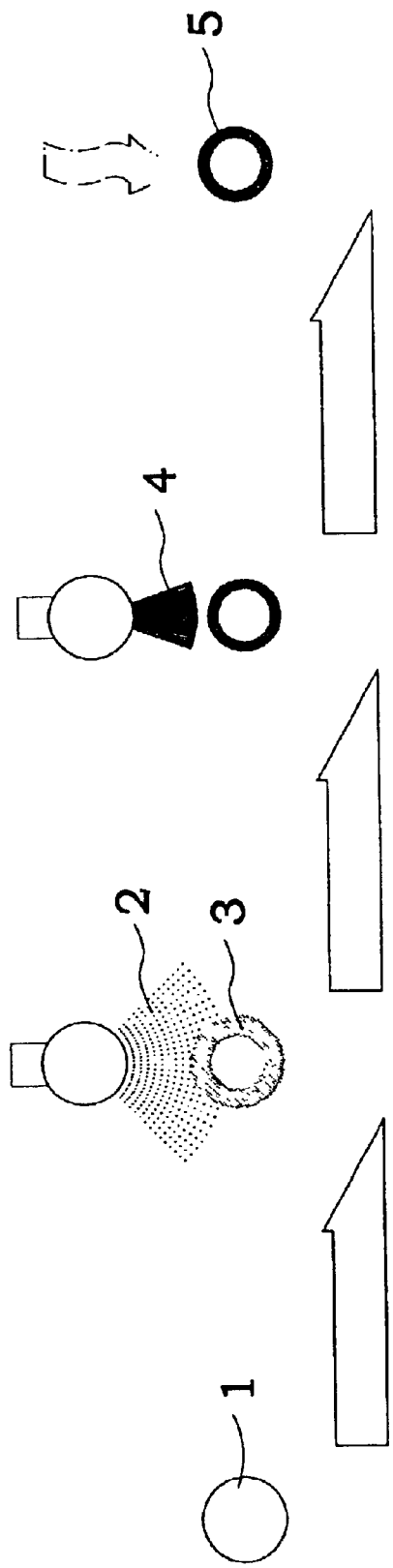
FIG. 1 is a schematic drawing showing the procedure of the operation of a preferred embodiment of the present invention.

Referring to FIG. 1, the method of the present invention comprises the steps of:

(a) selecting a polymer material that is degradable and absorbable in living beings, for example, polylactide, polyglycolid, polyglycolide/polylactide copolymer, glycolide/trimethylene carbonate copolymer, poly-β-hydroxybutyric acid, poly-β-hydroxypropionic acid, poly-p-dioxanone, poly(N-acetyl-β1,4-glucosamine), or polycaprolactone, and then forming the selected polymer material into a chipped matrix 1 by polymerization;

(b) using a high volatile solvent 2, for example, dichloromethane, chloroform, tetrahydrofuran or naphethalene to dissolve the surface of the chipped prepared matrix 1 thus obtained slightly, forming surface-dissolved chips 3;

(c) selecting an inorganic reinforced filler 4, for example, powder of hydroxyapatite, aluminum oxide, calcium phosphate, dicalcium phosphate, apatite, mixture of magnesium calcium phosphate and tricalcium phosphate, or mixture of hydroxyapatite and tricalcium phosphate, and then coating the prepared inorganic reinforced filler 4 onto the surface-dissolved chips 3, thereby forming a precursor 5.

Figure 2:
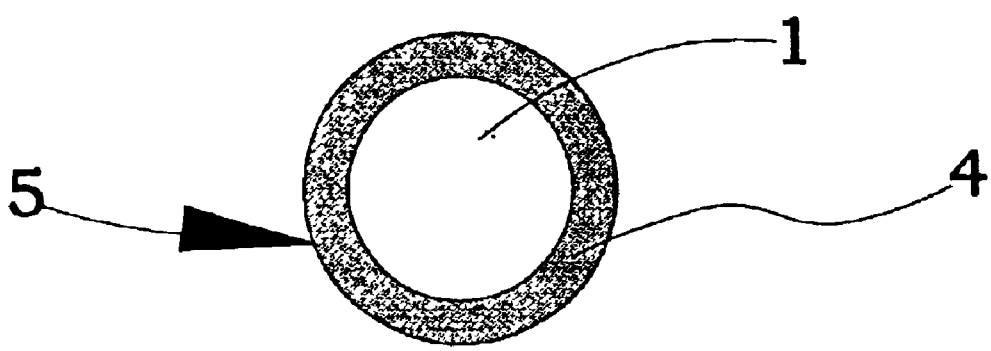
FIG. 2 is a sectional view showing the structure of a precursor made according to the preferred embodiment of the present invention.

FIG. 2 shows a precursor 5 obtained subject to the procedure mentioned above. As illustrated, the precursor 5 has a core of chipped matrix 1, and a covering of inorganic reinforced filler 4 coated onto the core of chipped matrix 1.

Figure 3:
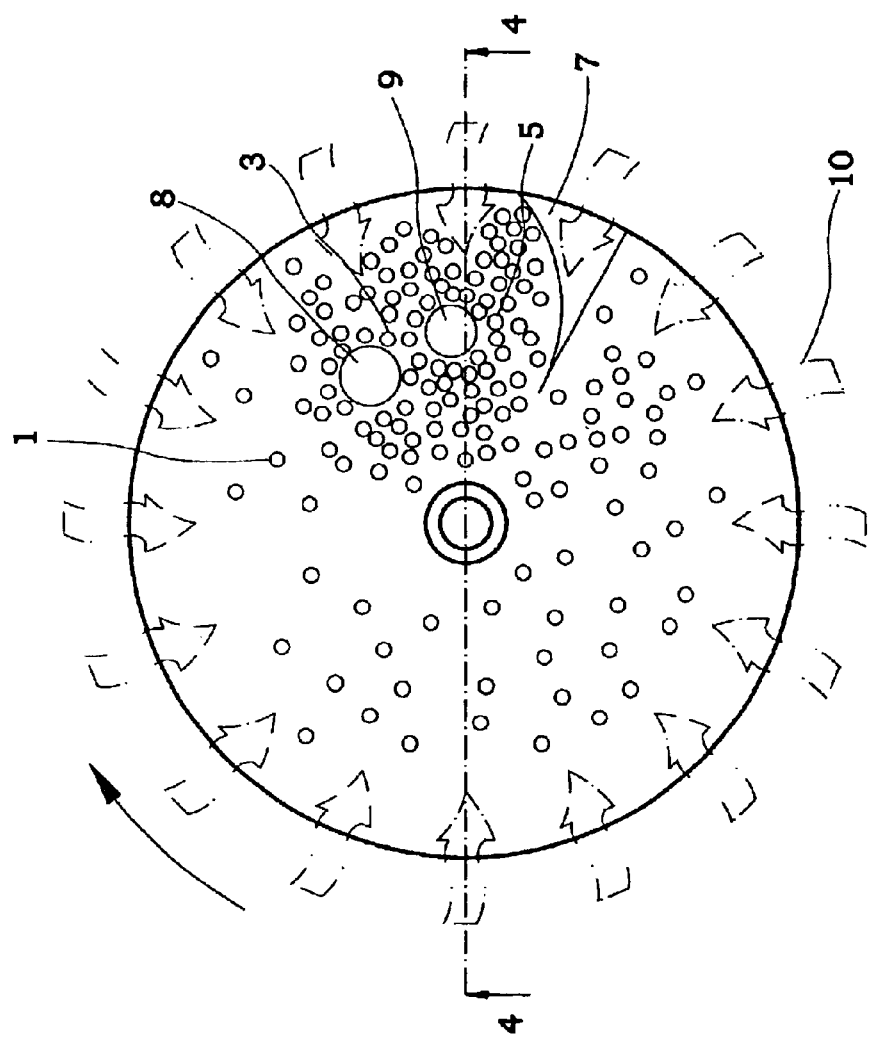
FIG. 3 is a top view of an apparatus used for the performance of the procedure according to the preferred embodiment of the present invention.
Figure 4:
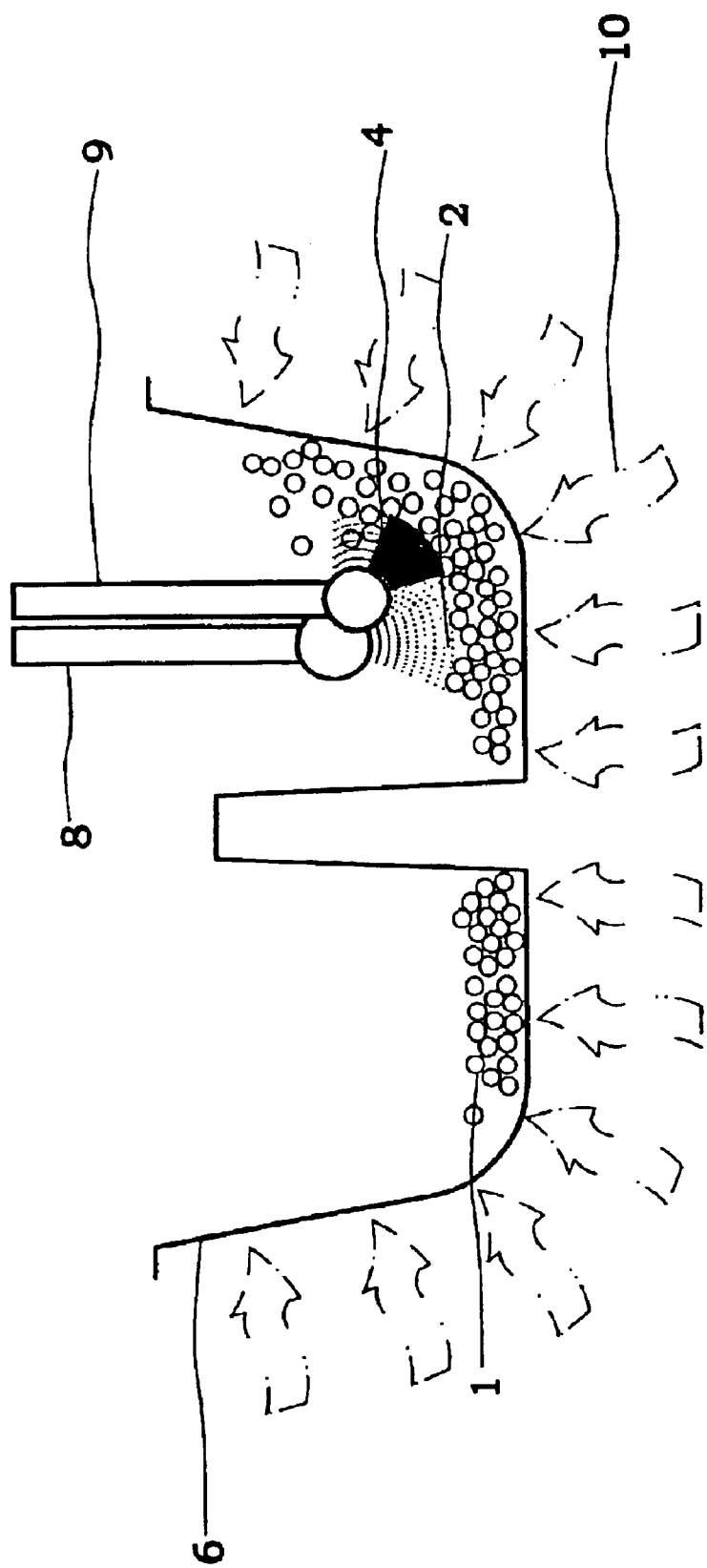
FIG. 4 is a sectional view taken along line 4—4 of FIG. 3.

The procedure mentioned above is performed in an enclosed chamber. FIGS. 3 and 4 show the apparatus used for the performance of the above-mentioned procedure. In FIGS. 3 and 4, the enclosed chamber is not shown. The so-called "enclosed chamber" can be defined in a container (not shown) having an openable top cover. The reference number 6 indicates a bowl-like rotary member having tiny through holes and being actuated to rotate by an external driving force. The prepared chipped matrix 1 is put in the rotary member 6. During rotation of the rotary member 6, the chipped matrix 1 are rotated and moved in and relative to the rotary member 6. A baffle 7 is provided inside the rotary member 6, and adapted for causing the chipped matrix 1 to turn in different directions. The reference number 8 indicates a first spray gun adapted for spraying the prepared solvent 2 onto the surface of the chipped matrix 1 to dissolve the surface of the chipped matrix 1, forming the above-mentioned surface-dissolved chips 3. The reference number 9 indicates a second spray gun adapted to spray the prepared powdered inorganic reinforced filler 4 onto the surface-dissolved chips 3, forming the desired chips, i.e., the precursor 5 mentioned above. The reference number 10 indicates forced currents of air adapted for accelerating the changing of the applied solvent into vapor. It is preferable to provide forced hot air to accelerate the changing of the applied solvent into vapor. According to the present invention, the desired chips, i.e., the above-mentioned precursor 5 is produced in the apparatus batch by batch. The outer shell, i.e., the covering of inorganic reinforced filler 4 of the precursor 5 has a thickness about 35% of the diameter of the precursor 5. The precursor made by the present invention has a coated surface of reinforced filler to enhance the structure strength thereof, so it is suitable for carry, storage and use of injection-molding and/or extrusion.

EXAMPLE

Materials used: poly-L-lactide ($\overline{Mw}$=104 kDa), dichloromethane, apatite powder ($\overline{Mw}$=1004.64 kDa)

Application: take 350 g poly-L-lactide of average molecular weight 140 kDa and then put it in the rotary member being rotated at 200–500 rpm. Connect the first spray gun to a solvent container containing 1 liter of dichloromethane. Operate the first spray gun to spray dichloromethane onto the surface of the chips of poly-L-lactide in the rotary member. Immediately, operate the second spray gun to spray prepared 150 g apatite powder of average molecular weight 1004.64 into the enclosed chamber, causing apatite powder of particle diameter about 1~3 μm to be uniformly covered on the surface-dissolved chips of poly-L-lactide. This procedure takes about 10~30 minutes. During the procedure, 30~50° C. hot air is continuously delivered to the inside of the enclosed chamber to dry the chips. When dried, the desired finished product is obtained.

When observed the finished product thus obtained, a layer of apatite covering of uniform thickness is tightly bonded to the core member of poly-L-lactide. When twisting the finished product with the hands, the layer of apatite covering does not drop from the cover member of poly-L-lactide. The precursor thus obtained can then be injection-molded into a biomaterial subject to the desired shape and size. The required three-step temperature control of the injection-molding procedure is at temperatures 150° C., 150° C., and 155° C. respectively. During injection-molding, the screw rod compression ratio is controlled at 1.1.

Figure 5:
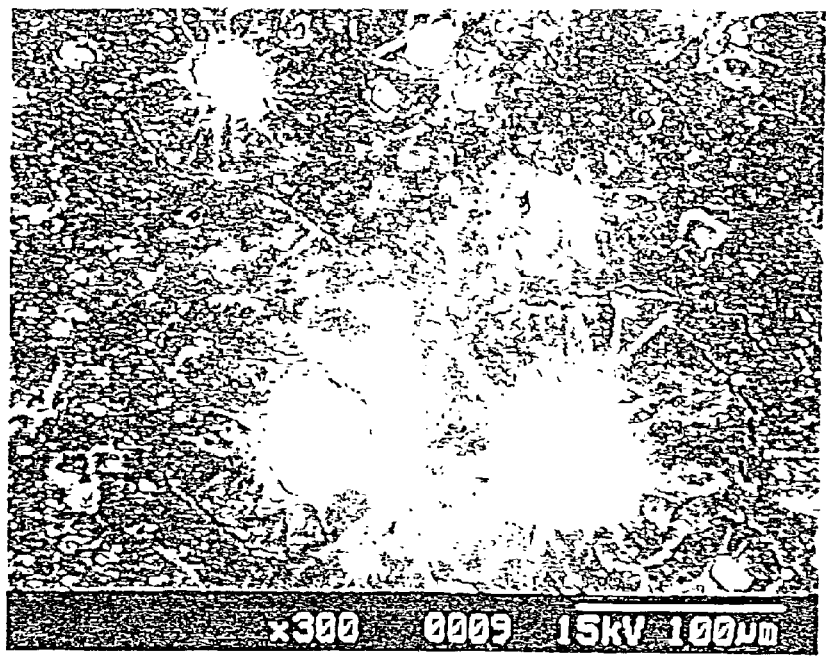
FIG. 5 is a schematic drawing of a compound material product constructed according to the prior art when viewed under an electron microscope.
Figure 6:
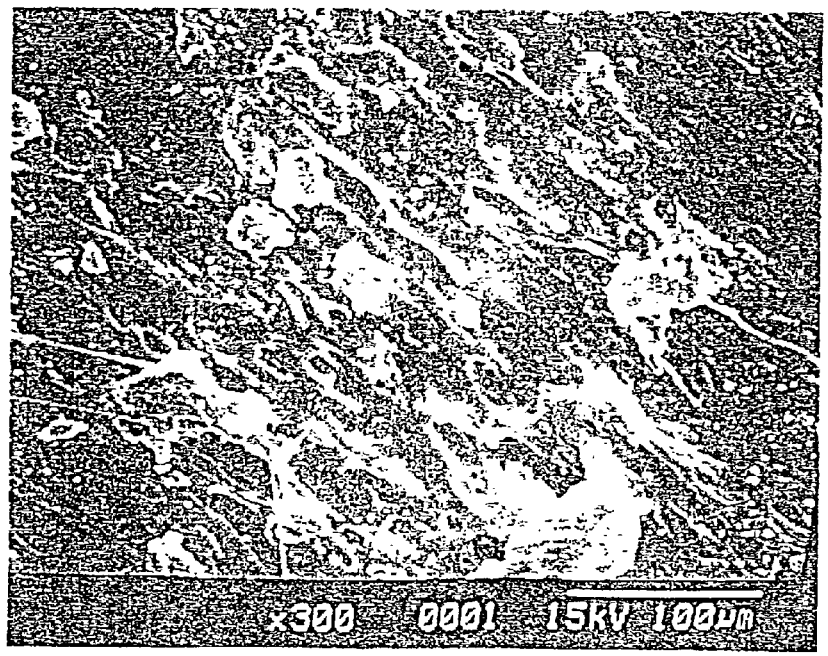
FIG. 6 is a schematic drawing of a compound material product constructed according to the present invention when viewed under an electron microscope.

As shown in FIG. 5 and FIG. 6, in comparison with the prior art method when viewed through a Scanning Electron Microscope (SEM), HA/PLLA compound material made from the precursors of the present invention by injection-molding shows uniform blending superior to that made according to the prior art method.

The method mentioned above is to produce the precursor by batch production, however it can be produced by continuation production.

The solvent used in the above-mentioned step (b) can be further added with the matrix, keeping the concentration of the matrix within about 1%~10%. For example, mixing dichloromethane with poly-L-lactide, forming a solution of concentration 2%. The solution is applied to the surface of the chipped matrix of poly-L-lactide 1. Dichloromethane solvent slightly dissolves the surface of the chipped matrix of poly-L-lactide 1, enabling poly-L-lactide of the solvent to be adhered to the surface of the chipped matrix. This effect accelerates the formation of dissolving layer at the surface of the chipped matrix.

The powdered inorganic reinforced filler used in the above-mentioned step (c) can be applied to the surface-dissolved chips to form the desired precursor by spreading or spraying. Alternatively, the powdered inorganic reinforced filler can be mixed in the solvent, and then applied to the surface-dissolved chips by a spray gun, i.e., powdered material can be mixed in the solvent prepared during Step (b), or the powder prepared during Step (c) can be added with a solvent.

The above-mentioned steps may be relatively combined or repeatedly applied. For example, dissolving the surface of the chipped matrix can be achieved by means of applying pure solvent, solvent containing a certain amount of the chipped matrix, solvent containing a certain amount of inorganic reinforced filler, or solvent containing a certain amount of chipped matrix and a certain amount of inorganic reinforced filler. A repeat use of two or three of the solvents mentioned above is also applicable.

The inorganic reinforced filler coating procedure can be achieved by means of applying pure powdered inorganic reinforced filler or mixture of inorganic reinforced filler and solvent to the surface-dissolved chips. Alternatively, the procedure can be achieved by means of applying both pure powdered inorganic reinforced filler and mixture of inorganic reinforced filler and solvent to the surface-dissolved chips, for example, applying solvent containing inorganic reinforced filler at first and then applying powdered inorganic reinforced filler.

In conclusion, the spirit of the present invention is to slightly dissolve chipped matrix with solvent, and then to coat slightly dissolved chipped matrix with reinforced filler, thereby forming a heterogeneous precursor for further processing into a biomaterial produce through an injection-molding processing, an extrusion processing or the like. Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method of making a compound precursor adapted to be further used in an injection-molding processing, an extrusion processing or the like, the method comprising the steps of:
   (a) selecting a biodegradable and bioabsorbable polymer material and then forming the selected polymer material into a chipped matrix;
   (b) using a solvent to dissolve the surface of said chipped matrix slightly; and
   (c) coating the surface-dissolved chipped matrix with a reinforced filler, thereby forming a heterogeneous precursor.

2. The method as claimed in claim 1, wherein said reinforced filler is a powdered inorganic material.

3. The method as claimed in claim 1, wherein the solvent used in step (b) contains a predetermined amount of said chipped matrix.

4. The method as claimed in claim 3, wherein the concentration of said chipped matrix in said solvent is within about 1%~10%.

5. The method as claimed in claim 1, wherein the solvent used in step (b) contains a predetermined amount of said reinforced filler.

6. The method as claimed in claim 1, wherein the reinforced filler used in step (c) is mixed with a solvent before application.

7. The method as claimed in claim 3, wherein the reinforced filler used in step (c) is mixed with a solvent before application.

8. The method as claimed in one of the claims from 1 through 7, further comprising a drying step of drying the heterogeneous precursor thus obtained.

9. The method as claimed in claim 8, wherein said drying step is to dry the heterogeneous precursor with hot air.

10. A method of making a compound precursor comprising the steps of:
    (a) selecting a biodegradable and bioabsorbable polymer material and then forming the selected polymer material into a chipped matrix; and
    (b) mixing a reinforced filler in a solvent to form a mixture, and then spraying said mixture onto said chipped matrix to dissolve the surface of said chipped matrix and to let said reinforced filler be coated on the surface of said chipped matrix, thereby forming the precursor.

11. The method as claimed in claim 10, further comprising a drying step of drying the precursor thus obtained.

12. The method as claimed in claim 1, wherein said polymer material is selected from the group consisting of polylactide, polyglycolid, polyglycolide/polylactide copolymer, glycolide/trimethylene carbonate copolymer, poly-$\beta$-hydroxybutyric acid, poly-$\beta$-hydroxypropionic acid, poly-p-dioxanone, poly(N-acetyl-$\beta$1,4-glucosamine), and polycaprolactone.

13. The method as claimed in claim 1, wherein said reinforced filler is selected from the group consisting of hydroxyapatite, aluminum oxide, calcium phosphate, dicalcium phosphate, apatite, mixture of magnesium calcium phosphate and tricalcium phosphate, and mixture of hydroxyapatite and tricalcium phosphate.

14. The method as claimed in claim 1, wherein said solvent is selected from dichloromethane, chloroform, tetrahydrofuran or naphethalene.

15. The method as claimed in claim 1, wherein the steps (a), (b), and (c) are performed in an enclosed chamber.

16. The method as claimed in claim 15, wherein said enclosed chamber is provided with a rotary member adapted for rotating said chipped matrix; said solvent and said reinforced filler are supplied by spraying during step (b) and step (c) respectively.

17. The method as claimed in claim 16, wherein a hot air source is provided below said enclosed chamber and adapted for providing hot air into said enclosed chamber to dry the precursor thus obtained.

18. The method as claimed in claim 16, wherein said rotary member is a hollow rounded rotary device having a plurality of through holes through the periphery thereof and a baffle disposed on the inside and adapted for causing said chipped matrix to turn in different directions upon rotary motion of said rotary member; a first spray gun is provided and adapted for applying said solvent to said chipped matrix; a second spray gun is provided and adapted for applying said reinforced filler to said surface-dissolved chipped matrix.

* * * * *